United States Patent [19]
Chin et al.

[11] Patent Number: 5,582,618
[45] Date of Patent: *Dec. 10, 1996

[54] SURGICAL CUTTING INSTRUMENT

[75] Inventors: Albert K. Chin, Palo Alto; Charles Gresl, San Francisco, both of Calif.

[73] Assignee: R.J. Surgical Instruments, Inc., Encinitas, Calif.

[ * ] Notice: The term of this patent shall not extend beyond the expiration date of Pat. No. 5,385,570.

[21] Appl. No.: 357,103

[22] Filed: Dec. 15, 1994

Related U.S. Application Data

[63] Continuation of Ser. No. 3,287, Jan. 12, 1993, Pat. No. 5,385,570.

[51] Int. Cl.$^6$ ................................................ A61B 17/32
[52] U.S. Cl. ........................ 606/170; 606/79; 128/751
[58] Field of Search ................................ 606/79, 83, 84, 606/170, 174, 167, 51, 52, 205–211; 128/750–755; 604/22

[56] References Cited

U.S. PATENT DOCUMENTS

| | | |
|---|---|---|
| 460,903 | 10/1891 | Woodward . |
| 1,493,240 | 5/1924 | Bohn . |
| 3,752,161 | 8/1973 | Bent . |
| 3,902,498 | 9/1975 | Niederer . |
| 4,201,213 | 5/1980 | Townsend . |
| 4,368,734 | 1/1983 | Banko . |
| 4,644,951 | 2/1987 | Bays . |
| 4,733,663 | 3/1988 | Farley . |
| 4,777,948 | 10/1988 | Wright . |
| 5,026,375 | 6/1991 | Linovitz . |

*Primary Examiner*—Michael Powell Buiz
*Assistant Examiner*—William Lewis
*Attorney, Agent, or Firm*—Baker, Maxham, Jester & Meador

[57] ABSTRACT

A surgical cutting instrument having jaws formed on the distal ends of an outer and an inner cutting member. A recess in the inner cutting member is provided for collecting chips of material. A removable sheath over the outer cutting member permits removal of chips. The sheath also functions to prevent tissue damage. In an alternate embodiment, a collection chamber is provided for storing collected chips of material.

19 Claims, 5 Drawing Sheets

SURGICAL CUTTING INSTRUMENT

This is a continuation of application Ser. No. 08/003,287 filed on Jan. 12, 1993, now U.S. Pat. No. 5,385,570.

FIELD OF THE INVENTION

This invention relates to a surgical instrument of the type that is used for nibbling or shearing away of bone or tissue during surgical procedures. It is particularly directed to such an instrument in the form of a rongeur that is useful in close or sensitive areas such as in the spine or cervical area.

BACKGROUND OF THE INVENTION

Currently there are many rongeurs that are adapted to cut, nibble or grip bone or tissue during surgical operations such as in spinal surgery. These instruments are configured to cut away the bone overlying the spinal cord during a laminectomy and a spinal decompression. Other uses include: in neurosurgery, to cut away the spine in the cervical area or in skull and brain surgery; in head and neck surgery, to remove bone in the areas of the nose and face.

One typical prior art rongeur is shown in U.S. Pat. No. 4,201,213 issued to Townsend. This device illustrates the basic components of such rongeurs, having a pair of cooperating, slidable cutting elements which are manually actuated by means of a pair of handles at its proximal end. A generally tubular movable cutting element includes therein a relatively fixed cutting element having a recess therein so as to define a footplate or anvil structure at its distal end. The footplate and sharp distal end of the movable cutting element cooperate to act as jaws and effectively cut bone or tissue placed therebetween. Because the blade edges on such rongeurs come into contact and rather quickly become dull through use, they have to be frequently resharpened. However, repeated resharpening after a time will cause misalignment of parts and therefore imperfect cutting. The subject prior art device includes a replaceable cutting tip in an attempt to alleviate this problem.

Another problem with rongeurs of this type results from the large forces that are generated when bone is compressed between the jaws of the rongeur. The large forces frequently cause failure of the metal of the footplate at its juncture with the axially directed fixed cutting element. In spinal surgery, a thin footplate is desired in order to be able to reach within the narrow spaces in the spinal canal. This necessity for a thin footplate exacerbates the weak footplate problem thus described.

Present rongeurs of this type also require that each bone chip produced by a cut be removed prior to the subsequent repetition. This is currently done by the surgical scrub nurse or surgeon wiping off the bone chip between each cut. This requires the surgeon to take his or her eyes off the surgical situs or working area during this cutting process, only to refocus on the situs after each bone chip has been removed. This process adds unnecessary time to the surgery. Each bone chip must be removed from the surgical field, in order to prevent obstruction or impingement on delicate structures such as the spine or brain.

One attempt to solve the chip removal problem is shown in U.S. Pat. No. 3,902,498 issued to Niederer. With this device, an elongated storage recess is formed in the inner cutting element so that bone chips from a number of cuts may be stored therein prior to being ejected from a side discharge opening. However, the storage capacity is limited. The bone chips may also be ejected into the surgical field.

Still another deficiency with the above prior art devices is that tissue in the operation situs may be damaged by reciprocation of the cutting members, since they do not have any means for shielding the tissue from their movement. Still another undesirable feature of many prior art rongeurs is that it crushes the bone chip being removed as it cuts the chip away from the bone.

SUMMARY OF THE INVENTION

The present invention involves a cutting instrument that incorporates a shearing action between the cutting elements similar to that of a paper hole punch. In an alternate embodiment, it also includes a visible collection chamber in its handle for capturing and storing bone chips. This collection chamber provision not only keeps the chips away from the operation situs, but provides samples of bone for specimen analysis and pieces for bone grafts. This results from the fact that this instrument shears or cuts the bone chips, rather than crushing them.

In this embodiment, a removable end cap in the handle is provided so that bone chips may be selectively stored and removed.

Also included in yet another embodiment is an indicator rod which extends further from the rearward end of the instrument housing as each cut is made, due to the action of the bone chips moving rearwardly within a recess in a cutting element. The indicator may serve the dual purpose of visually informing the surgeon when the cutting edge is dull, as well as when the recess is full. The rod may then be used to expel the chips forwardly after the instrument has been removed from the operation situs. Shield means may also be provided to protect delicate tissues such as dura matter from being caught, torn or abraded by the cutting elements.

In the preferred embodiment, the surgical cutting instrument comprises a pair of cutting elements in the form of an elongated tubular outer member having a passage therethrough. An elongated member projects from the distal end of the outer member and extends through the passage to a point where its proximal end is fixed in a housing. The inner member forms an angularly directed footplate which cooperates with the distal end of the outer member to form jaws which operate to shear bone or tissue placed therebetween.

The outer member is relatively movable with respect to the fixed inner member to achieve this shearing by means of a pistol grip and lever arrangement which may be manually actuated. An elongated, removable shield of material such as clear plastic is also provided, so that the bone chips may be retained in the instrument until it is desired to remove them. A latch mechanism integral with the grip is provided, in order to permit removal and locking of the shield.

The basic operation of the device is that as the lever is reciprocated, the jaws take sequential bites of bone to produce chips that are forced to move in the rearward direction in a recess in the inner member. Each chip in turn forces the previous chips in the rearward direction.

In an alternate embodiment, to facilitate this movement, the outer member may be stepped to provide a larger diameter passage as the chips move rearwardly. Alternatively, serrated rearwardly facing teeth may be provided on the inner member to "ratchet" the bone chips in the rearward direction with each cut.

Because the recess extends some distance along the length of the inner member, stabilization may be required to prevent misalignment of the cutting members due to the large forces incident to cutting hard bone material. To accomplish this stabilization, a spacer block of hard material is placed within the passage to serve to position the inner and outer members. The spacer block is initially placed at the distal end of the outer cutting member within its passage. This spacer block is pushed in the rearward direction as bone is cut, with the cut bone chips continuing to maintain the desired stability due to their hardness and relative incompressibility.

Alternatively, a rod in the passage can restrain misalignment.

Another embodiment of the invention is with respect to the moving bottom edge of the outer tubular member. In order to minimize damage to tissue in the operation situs, a protective shield is provided. With this embodiment, a thin tubular shield which may be of plastic material projects from the housing and closely surrounds the outer cutting member distally to the footplate. This shield covers the moving bottom cutting edge of the tubular outer member. In order to move the shield rearwardly from the footplate, thus conserving the small dimensions of the footplate portion for easy cutter placement during surgery, the outer member may be undercut or stepped back.

In still another embodiment of the shield, a thin elastromeric strip is bonded or otherwise attached at its ends to the bottom of the footplate and to the outer cutting member, respectively, approximately 1 cm. proximal to its free edge. The elastromeric strip is prestretched upon full advancement of the outer member along the inner member.

Yet another means for guarding against tearing of tissue is the attachment of a tubular section of plastic material around the distal end of the outer member so that it extends rearwardly from and protects the sharp cutting edge of that member. The relatively soft bottom edge portion of this section hugs the surface of the inner cutting member and functions similar to that of a windshield wiper blade on an automobile windshield. During advancement of the outer cutting member, the edge of the section pushes away tissue that may be caught by the moving tube and seals against the bottom surface of the inner cutting member. The section may be made up of a short length of heat shrinkable polyolefin plastic tubing that is heat shrunk over the distal end of the outer cutting member.

In order to facilitate viewing of the cutting site, the footplate may be conveniently angled with respect to the inner member rod portion. To prevent hard bone from slipping out of the jaws, a slight back cut may be made in the back face of the footplate so as to create a rearwardly facing rib. Alternatively, a bore may be made into or through the back face to provide a sharp circular ridge that aids in gripping.

The entire instrument may be disposable.

BRIEF DESCRIPTION OF THE DRAWING

The objects, advantages, and features of the invention will be more readily perceived from the following detailed description, when read in conjunction with the accompanying drawing, in which.

DESCRIPTION OF THE PREFERRED EMBODIMENTS

Figure 1:
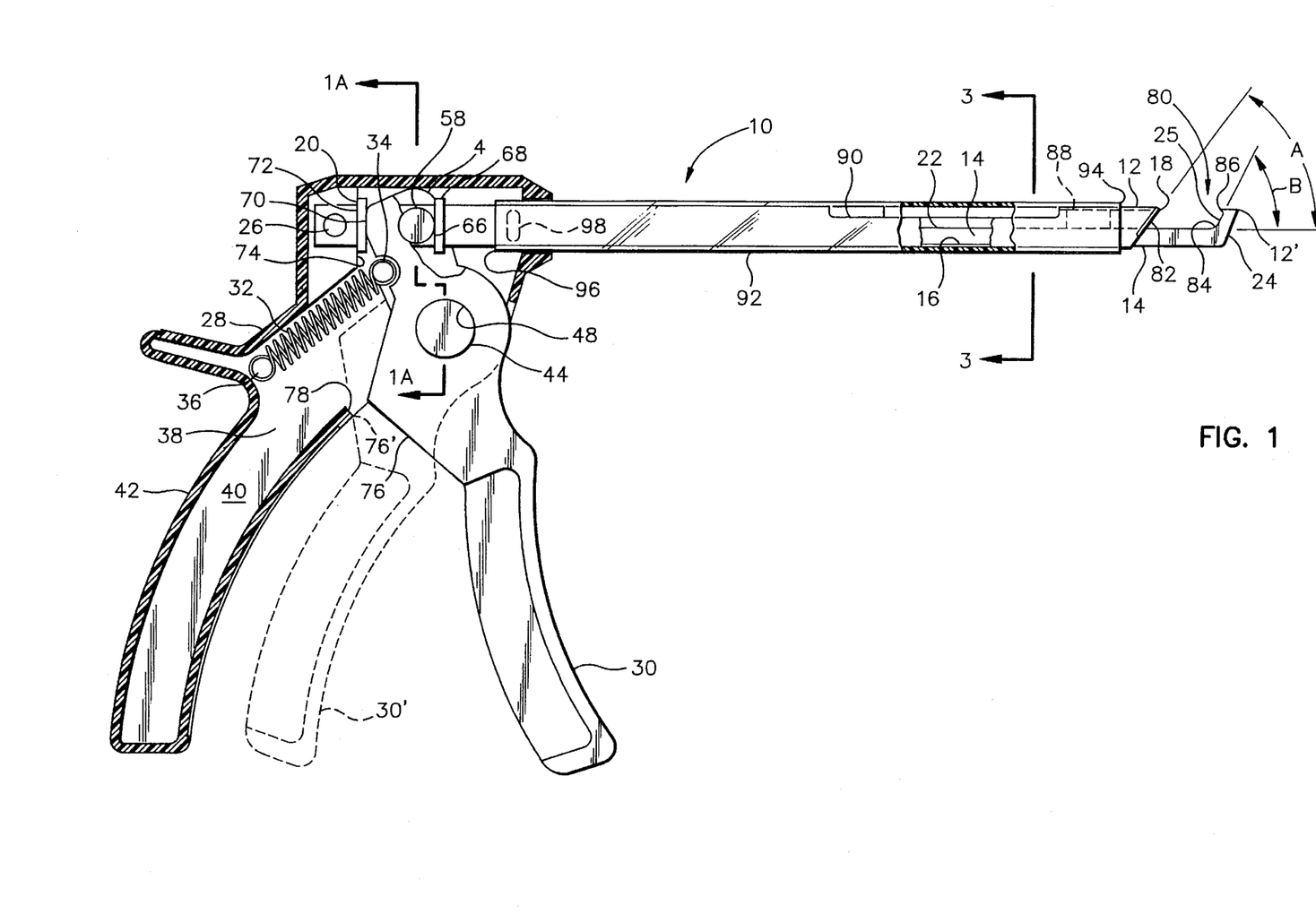
FIG. 1 is a side elevation view in partial cross-section showing a preferred embodiment of the surgical cutting instrument of this invention.
Figures 2, 3:
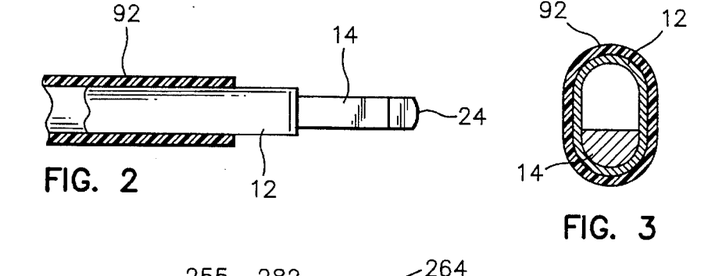
FIG. 2 is a top plan view of the distal end portion of the cutting instrument in FIG. 1.
FIG. 3 is a cross-sectional view taken along lines 3—3 in FIG. 1.
Figure 3A:
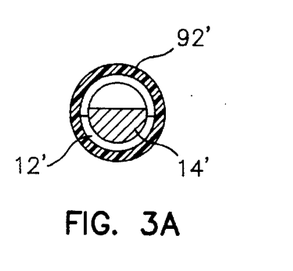
FIG. 3A is an alternate embodiment wherein the cross-section is circular rather than oval.

Turning to FIG. 1, the preferred embodiment of the surgical cutting instrument invention is shown generally at 10. The instrument comprises outer and inner cutting members 12, 14, respectively. Outer cutting member 12 is generally tubular in cross-section and defines passage 16 therethrough having a generally oval shape, as seen in FIG. 3. It is to be understood that the oval shape is for sake of convenience. As seen in FIG. 3A, the shape of the cross-section may be circular, for example.

Outer cutting member 12 includes an inlet opening at its distal end. Circumferential edge 18 which defines the opening forms one cutting element. This edge extends axially and is curved or arcuate at the outermost portion and is at an angle "A" of about 45 degrees to the longitudinal axis of the outer member. Angle "A" could be less than 45 degrees, but preferably not much greater than that angle. Outlet opening 20 is located at the proximal end of the outer member. Inner cutting member 14 is in the form of an elongated rod of generally tubular cross-section having recess 22 extending part way along the length of the cutting member and defining footplate 24 having a rearward facing anvil 25 at its distal end. The operative cutting element portion is the peripheral edge of anvil 25 which is at an angle "B" with respect to the aforementioned axis. This angle "B" can vary over a relatively wide range, but it must be greater than angle "A" so that a shearing or "scissors" cutting action occurs as edge 18 moves into close engagement with anvil 25. The cutting action will start at the top (in FIG. 1) and continued movement of element 12 results in a slicing action down the mating sides of edge 18 and anvil 25. Cutting members 12, 14 may be made of stainless steel or other suitable material.

Inner cutting member 14 is fixed at its proximal end by means of pin 26 which extends laterally therethrough and is secured at each of its ends to housing 28. Outer cutting member 12 is reciprocated alternately in a longitudinal direction by means of hand manipulation of elongated lever 30 from the fully retracted position shown to a fully advanced position indicated by dotted lines 30' against the rearward biasing force of coil spring 32. Any other effective type of biasing structure may be used.

Figures 1A, 1B, 1C, 1D, 1E:
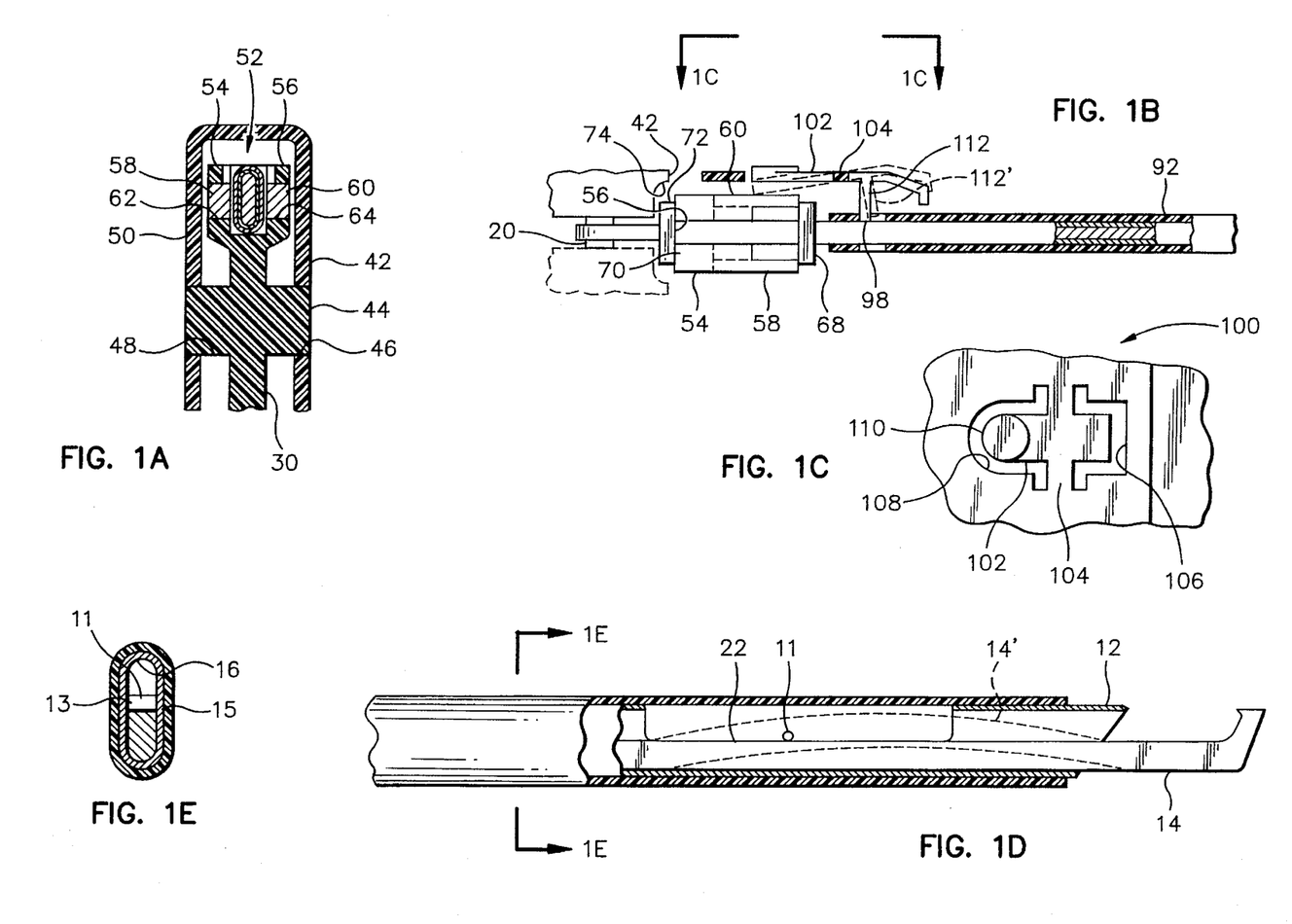
FIG. 1A is a cross-sectional elevational view taken along the lines 1A—1A in FIG. 1.
FIG. 1B is a partial top plan view of the proximal end portion of the cutting instrument of FIG. 1.
FIG. 1C is a partial, inverted side elevation taken along lines 1C—1C in FIG. 1B.
FIG. 1D is a partial side elevation view of the distal portion of the cutting instrument of FIG. 1 illustrating a means for preventing misalignment of the jaws.
FIG. 1E is a cross-sectional elevational view taken along lines 1E—1E in FIG. 1D.

Coil spring 32 is, in turn, fixed at its ends to pins 34, 36. Pin 34 is integrally molded on lever 30, whereas pin 36 is integrally molded on inner wall 38 within chamber 40 formed between the hollow, identical pistol grip halves of housing 28. Both housing 28 and lever 30 may be made of polycarbonate plastic material. Lever 30 is pivotally movable about integral shaft 44 fixed therein, as best seen in FIG. 1A. As seen in this figure, the opposite ends of integral shaft 44 are rotatable within bores 46, 48 in grip halves 42, 50, respectively.

Referring again to FIG. 1A, yoke 52, having a pair of bifurcated arms 54, 56, is integrally formed in the upper end of lever 30. Lever 30 is pivotally movable about integral shaft 44 so as to transmit motion to outer cutting member 12 by means of a pair of cylindrical metal bearing members 58, 60 which are press fit into accommodating bores 62, 64 in arms 54, 56, respectively.

As best seen in FIG. 1, each arm and each bearing member contacts and transmits force to a rectangular bearing plate which is fixed to outer cutting member 12. For example, bearing member 58 having a line of contact 66 at its arcuate forward side is in contact with forward bearing plate 68. As seen in this figure and in FIG. 1B, the similarly arcuate rearward side 70 of each arm is in contact with similar rearward bearing plate 72. That is, arms 54, 56 contact bearing plate 72 and transmit the force of spring 32 thereto in order to move outer cutting member 12 to its fully retracted position shown in contact with integrally molded wall stops.

In the opposite direction, edge 76 of lever 30, when in position 76', contacts ridge 78 within handle 42 so as to stop the movement of lever 30 at position 30'. In this fully articulated position of lever 30, outer cutting member 12 will have moved forwardly to position 12' covering footplate 24. Jaws shown generally at 80 are formed by angled forward cutting edge 82, which is beveled so as to present a sharpened line of contact with the peripheral edge of anvil 25. Anvil 25 has angled proximal wall 84 and generally rearwardly directed sharp point 86 at its upper extremity to aid in gripping bone material or the like. As is apparent, anvil 25 is shaped and dimensioned to closely fit within opening 18 so as to shear material placed between jaws 80.

Figures 8, 9:
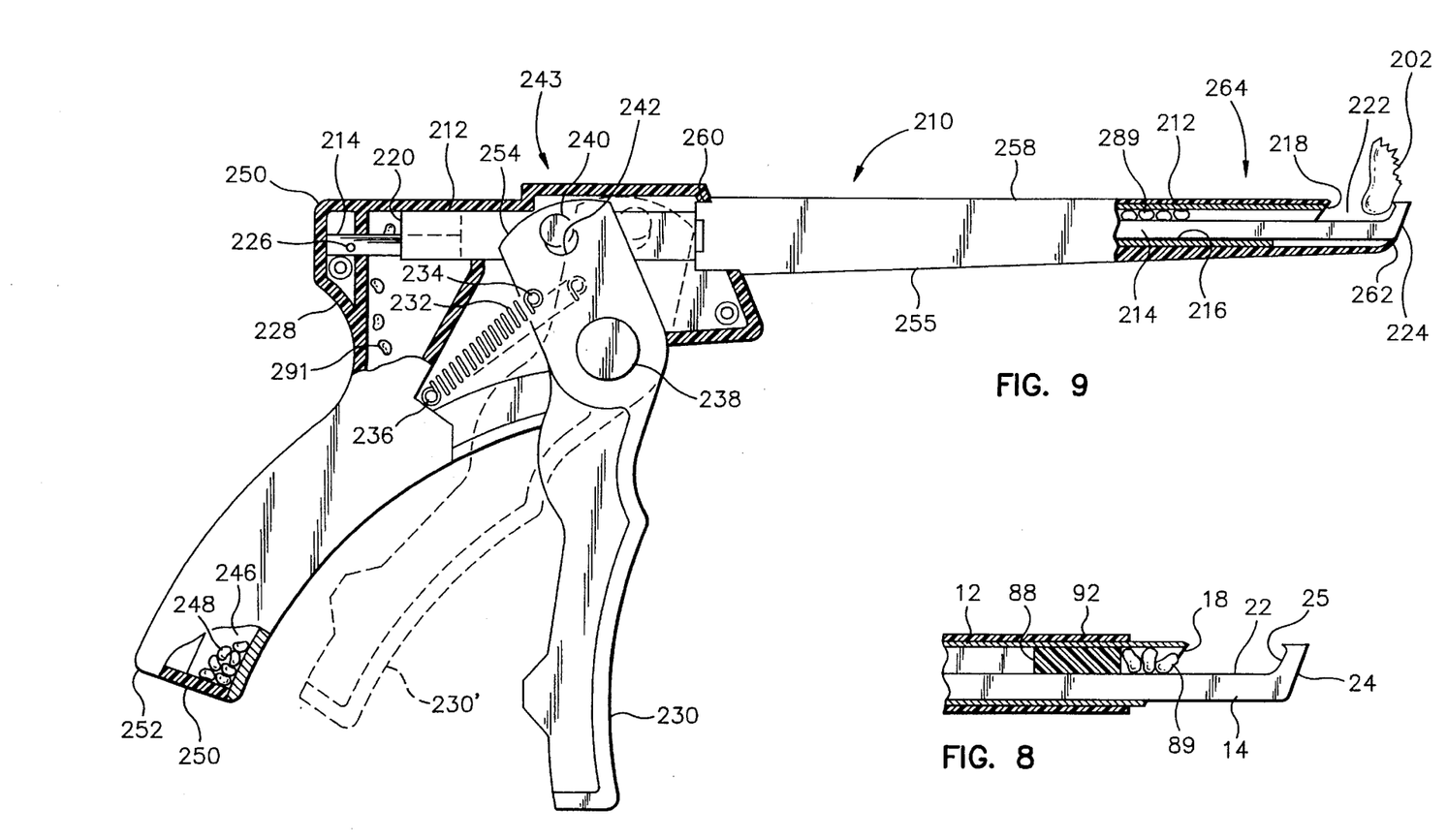
FIG. 8 is a view showing an alternate embodiment including a stabilizing plug.
FIG. 9 is a side elevation view in partial cross-section showing a second embodiment of the surgical cutting instrument having a collection chamber in the handle.

As each bite of material is taken, it is in turn forced back into recess 22. If desired, and as best seen in FIG. 8, a closely fitting spacer block 88 of plastic material may initially reside just inside opening 18 in order to prevent unwanted misalignment of the jaws until bites of cut material occupy the same space and perform the function of the block. The block is pushed in a rearward direction by each succeeding bite 89.

Elongated side opening 90 is cut part way through the top of outer cutting member 12 to permit periodic lateral removal. Until such removal, the bites are retained in recess 22 by means of clear plastic shield 92 which closely fits around outer member 12 and extends from just short of cutting edge 82 to within the housing, but spaced from plate 68 when in the position shown in FIG. 1. Shield 92 is of generally tubular configuration having distal and proximal open ends 94, 96, respectively. Near the proximal open end 96 is located vertical, elongated slot 98 through the wall of shield 92.

As may be seen in FIGS. 1B and 1C, a latch mechanism shown generally at 100 is formed in the side of pistol grip half 42. The latch mechanism is molded into the grip half and comprises generally elongated member 102 parallel to and flush with the grip half 42. The member as well as an integral vertically oriented pivot 104 is formed by means of slots 106, 108 through the grip wall.

Raised cylindrical pushbutton 110 is formed on the proximal end of elongated member 102 to facilitate pressing by the finger of an operator from a lateral direction for locking and unlocking the shield. In doing so, the elongated member rotates about pivot 104, and laterally projecting tongue member 112 which projects in a traverse, inward direction, is moved from a locked position within slot 98 to unlocked position 112' outside of slot 98. In this latter position, shield 92 may be removed from or installed on the device. Because the plastic material of the grip 42 has a "memory," latch mechanism 100 will automatically return to the condition wherein elongated member 102 is parallel and flush with grip 42.

Turning to FIGS. 1D and 1E, there is shown an alternate solution to the misalignment problem. With this solution, a small rod or pin 11 is fixed at its opposite ends 13, 15 to the inner wall of outer member 12. By locating rod 11 closely adjacent to inner member 14 within recess 22, the possibility of the inner member bowing, such as shown at 14', is eliminated.

A second embodiment of the instrument, which includes a collection chamber in the handle, will now be described, with reference to FIG. 9. Similar to the preferred embodiment, the instrument comprises outer and inner cutting members 212, 214, respectively. Outer cutting member 212 is generally tubular in cross-section, having passage 216 therethrough. At the proximal end is outlet opening 220. Inner cutting member 214 is in the form of a generally cylindrical elongated rod having recess 222 extending the length of the cutting member from footplate 224 at its distal end. Cutting members 212, 214 may be made of stainless steel material.

Inner cutting member 214 is fixed at its proximal end by means of pin 226 to housing 228. Outer cutting member 212 is reciprocated alternately in forward and rearward directions by means of hand manipulation of elongated lever 230 from the fully retracted position shown to fully advanced position 230' indicated by dotted lines. Lever 230 moves rearwardly against the biasing force of coil spring 232. Coil spring 232 is, in turn, fixed at its ends to pins 234, 236. Both housing 228 and lever 230 may be made of polycarbonate plastic material.

Lever 230 is pivotally movable about pivot 238 so as to transmit motion to outer cutting member 214 by means of laterally directed rods, one of which is shown at 240 affixed to member 212 and loosely passing through aperture 242 through arm 254. Arm 254 is one of two making up yoke 243 in the upper end of lever 230, somewhat in the manner of yoke 52 in FIG. 1A.

The hollow pistol grip handle, which may be transparent to enable viewing of the contents, includes collection chamber 246 therein for containing bone chips 248. The chips are removable by means of end cap 250 which may be unscrewed from heel end 252. In order to reduce damage to surrounding tissue, tubular shield 255 of thin plastic material is provided around the extended lengths of the cutting members. The shield is dimensioned to loosely fit around the outer cutting member 212 from the forward end of housing 228 to the distal end of the cutting members. Exterior surface 258 of shield 255 tapers slightly from its proximal end 260 to its distal end 262.

Figure 4:
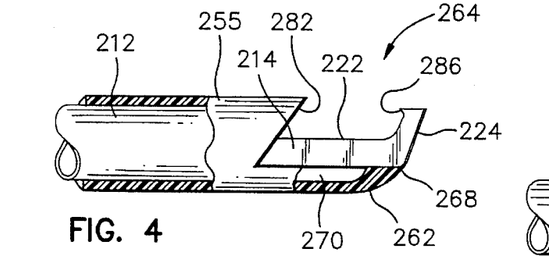
FIG. 4 is an enlarged side elevation view in partial cross-section of the distal end of the surgical cutting instrument of FIG. 1 showing details of the protective shield alternate embodiment.

As best seen in FIG. 4, shield 255 and a pair of cutting jaws 264 are formed between distal cutting edge 282 of outer member 212 and footplate 224. As seen in this figure, shield 255 is broken away at its distal end to expose jaws 264. Distal curved end 268 of the shield is bonded to fixed inner member 214. The bottom of cutting edge 282 will reciprocate within arcuate chamber 270 defined between shield 255 and inner cutting member 214.

Figure 4A:
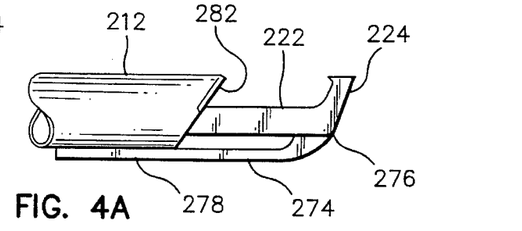
FIG. 4A is a view similar to FIG. 4 showing a second alternate shield embodiment in the form of an elastromeric strip.

Turning to FIG. 4A, there is shown a first embodiment of the shield of FIG. 4. With this embodiment, the shielding function is provided by thin elastomeric strip 274, which is bonded at its ends 276, 278 to the inner and outer cutting members. Strip 274 is bonded or otherwise attached approximately 1 cm. proximal to its free. cutting edge 282. The strip is prestretched such that it remains partially stretched upon full advancement of outer member 212.

Figure 4B:
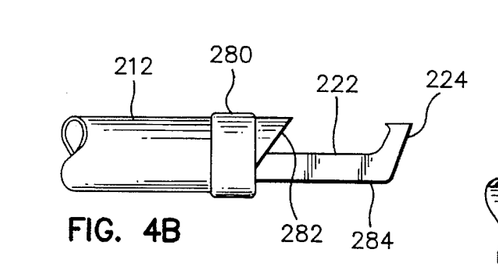
FIG. 4B is a view similar to FIG. 4 showing a third alternate shield embodiment in the form of a heat shrunk tubular section.

FIG. 4B shows a further alternate embodiment of the shield of FIG. 4. With this embodiment, a short section of plastic tubing 280 is shown around outer member 212 at its distal end so as to cover and protect the bottom portion of cutting edge 282. Plastic tube section 280 may be of heat shrinkable polyolefin material, which is shrunk over the outer member to tightly fit therewith. During advancement of outer cutting member 212, the soft lower edge of the tubing will closely contact and wipe underside 284 of inner member 214, acting similar to the wiper blade of an automobile windshield wiper.

Figure 4C:
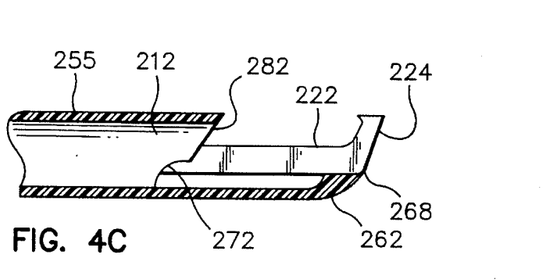
FIG. 4C is a view similar to FIG. 4 showing a fourth alternate embodiment with the outer cutting member cut away to permit a longer area of bonding of the shield to the inner cutting member.

In an alternate embodiment shown in FIG. 4C, the bottom portion of cutting edge 282 of cutting member 212 is cut away in arcuate recess 272 to enable distal end 262 of shield 255 to have a wider area of bonding contact at its distal end 268. This enhances the strength of the bond.

Figure 4D:
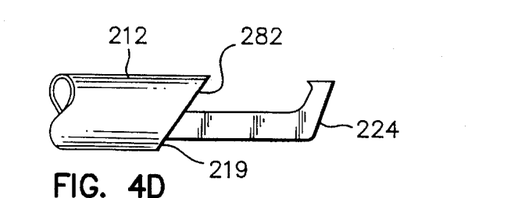
FIG. 4D is a view similar to FIG. 4 showing a fifth alternate embodiment having a radius on the lower portion of the outer member.

FIG. 4D shows an alternate embodiment wherein a radius 219 is formed on the lower portion of outer member 212 in lieu of a shield. This radius prevents damage to tissue caused by movement of the outer member thereover.

Figure 7:
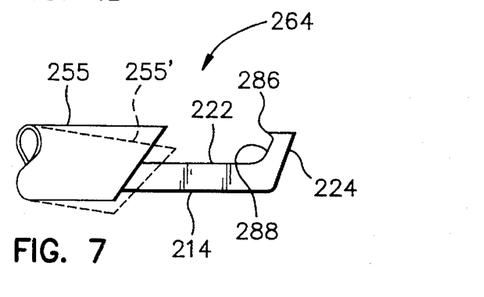
FIG. 7 is a side elevation view of the distal end of the cutting instrument illustrating misalignment that could occur due to forces generated during cutting hard bone.

Because large forces generated by cutting hard bone tend to cause the bone to slip off jaws 264 as seen in FIG. 7, means are provided to counteract this tendency. This takes the form of a sharp edge 286 on the rearward facing side of footplate 224. This edge may be formed by scooping out an arcuate lateral cut 288 in the same face of the footplate.

Figures 5, 6:
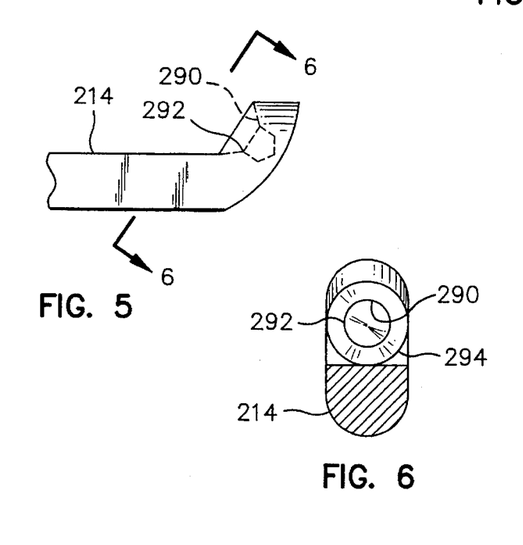
FIG. 5 is a side elevation view of an alternate embodiment of the distal end of the inner cutting member.
FIG. 6 is a view taken along lines 6—6 in FIG. 5.

In an alternate embodiment shown in FIGS. 5 and 6, bore 290 may be drilled into (as shown) or through (not shown) the rearwardly facing face of footplate 224. The bore may be counterbored as at 292 to produce sharp circular edge 294 that aids in gripping.

Returning again to FIG. 9, the operation of cutting instrument 210 will be briefly described. The instrument is first moved until a piece of material such as bone 202 is positioned between jaws 264. Lever 230 is then repeatedly manually actuated in the rearward direction. It is returned to its initial position by spring 232. In doing so, outer cutting member 212 is repeatedly reciprocated in a distal and proximal direction with respect to inner cutting member 214. The shearing action causes a series of bone chips 289 to progressively move toward and out the outlet opening 220 to drop as at 291 into collection chamber 246. Periodically, the chips may be removed through screw-out plug 250 in heel 252 of housing 228.

Figure 10:
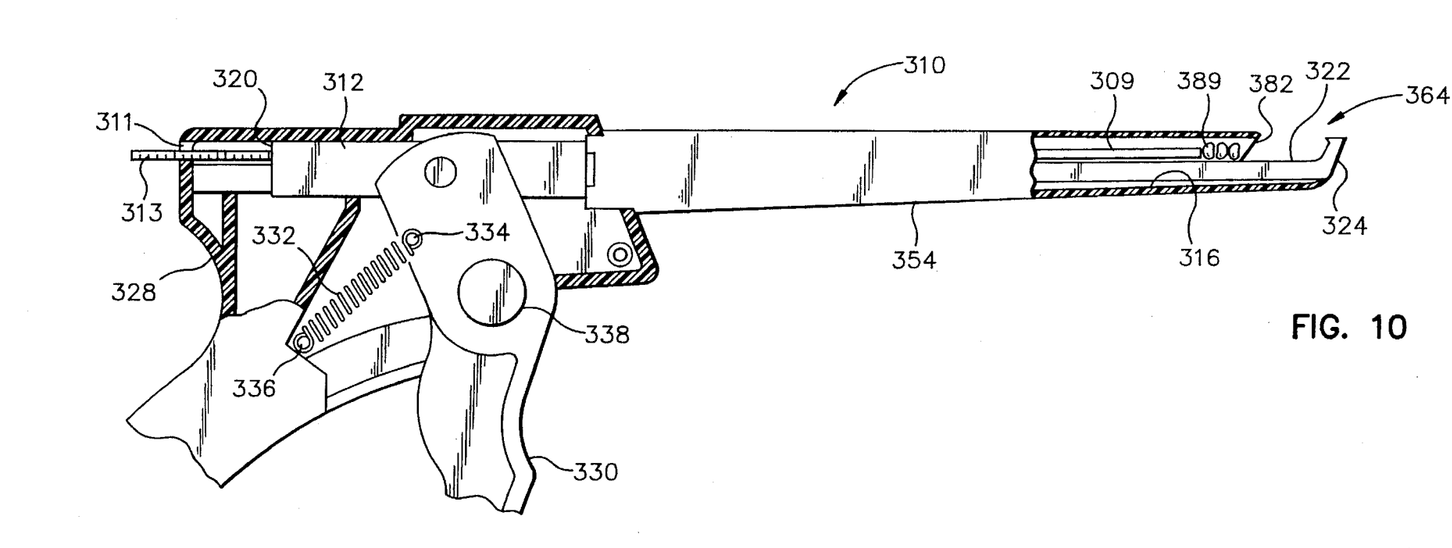
FIG. 10 is a side elevation view in partial cross-section of another alternate embodiment of the surgical cutting instrument of FIG. 9.

A further embodiment is shown in FIG. 10. This embodiment is similar, except that it does not include a collection chamber. Rather, it has elongated ejector rod 309 which is of a length to extend slightly out of aperture 311 in the rearward side of housing 328 while at the same time being flush with cutting edge 382 when jaws 364 of the instrument are in their open position. As each cut is made, the series of bone chips 389 thus produced will force ejector rod 309 in the rearward direction.

Indicia 313 on the proximal end of the rod allow visual indication of the number of cuts, since such are proportional to length. When it is desired to eject the collected bone chips, the instrument is removed from the operation situs and ejector rod 309 is manually pushed in the forward direction.

Figure 11:
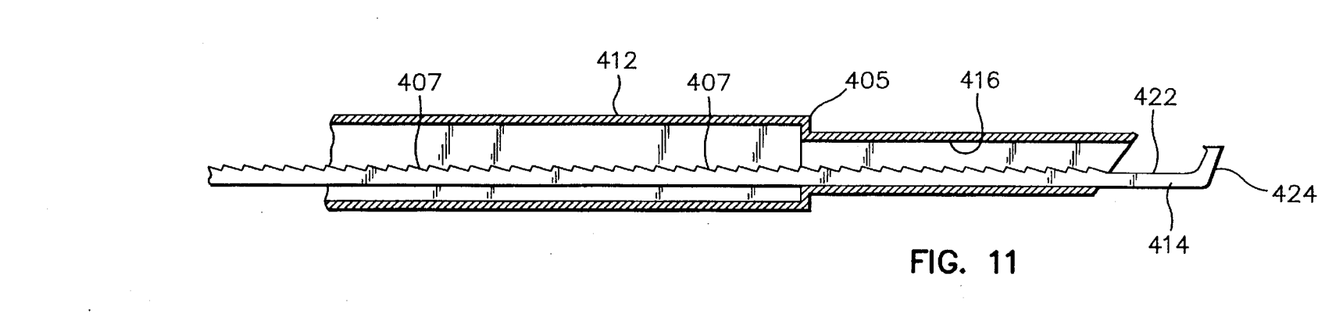
FIG. 11 is a side elevation cross-sectional view of an alternate embodiment of the inner and outer cutting members.

Because bone chips sometimes become jammed in passage 316, two solutions may be used either solely or in combination to solve this problem. As seen in FIG. 11, outer member 412 may be stepped as at 405 to produce wider inner passage 416 rearwardly of the step.

Another approach is to include a plurality of rearwardly facing serrations or teeth 407 on the surface of recess 422 for substantially its entire length. These teeth have a shallow forward facing ramp portion followed by an abrupt rearward facing ramp portion so as to provide a ratchet action on the bone chips as the members are reciprocated.

One important feature of the invention is that by employing the sharp edged outer tubular cutting member the bone chips are formed by cutting rather than by a combination of cutting and crushing. Many prior rongeurs did not have a space for the severed bone chips to easily go as they were severed, so they were crushed between the cutting faces as the severing action was completed.

It is to be understood that while the invention has been described above in conjunction with the preferred and alternate embodiments, the description and examples are intended to illustrate and not limit the scope of the invention, which is defined by the scope of the appended claims. In view of the above description, it is likely that modifications and improvements will occur to those skilled in the art which are within the scope of the accompanying claims.

What is claimed is:

1. A surgical cutting instrument comprising:

a housing;

an elongated fixed cutting member having a proximal end and a distal end and fixed at said proximal end to said housing, an axially directed fixed cutting edge on said a distal end directed toward said proximal end, and a recess adjacent said fixed cutting edge;

an elongated moveable cutting member reciprocally mounted on said fixed cutting member and having a distal end and a proximal end, an axially extending moveable cutting edge formed on said distal end and extending away from said proximal end toward said fixed cutting edge, said moveable cutting member being movable into shearing engagement with said fixed cutting edge and having an axially directed passage therein defining an inlet opening in said distal end, said cutting edges of said fixed and moveable cutting members being inclined toward one another and so configured as to produce a concentrated initial shearing action and a continuing progressive shearing action on bone placed between said cutting edges and thereby produce a chip of bone for each reciprocation of said first cutting member, wherein each said chip is deposited in said recess and moved into said passage through said opening and moves rearward with each reciprocation; and means on said housing for reciprocally moving said moveable cutting member with respect to said second cutting member in a first, forward direction and in a second, rearward direction.

2. The surgical cutting instrument of claim 1 further comprising sheath means on said housing covering at least a portion of said moveable cutting member so as to prevent damage to tissue in the region of the operation situs due to movement of said moveable cutting member, said sheath means not extending beyond the distal end of said fixed cutting member.

3. The instrument recited in claim 2, wherein said sheath means comprises a generally tubular shield fitted around said moveable cutting member, and means defining an opening in said moveable cutting member so as to permit removal of bone chips from said recess.

4. The instrument recited in claim 3, wherein said means defining an opening is a side opening and wherein said shield is of a length so as to normally cover said side opening whereby bone chips are thereby prevented from being removed through said means defining an opening.

5. The instrument recited in claim 2 wherein said sheath means comprises a section of plastic tubing close fitted onto the distal end of said moveable member in such a manner as to prevent the distal end of said member from touching and damaging tissue in the region of the operation situs.

6. The instrument recited in claim 1, and further comprising biasing means operatively connected to said means for moving said moveable member with respect to said fixed member for normally urging said means for moving to return to an initial position prior to producing said shearing action.

7. The instrument recited in claim 1, wherein said means for moving comprises a generally elongated lever, a lever pivot on said housing, said lever defining a pair of opposite ends and being rotatably mounted intermediate its ends on said pivot, means operatively connecting one of said lever ends to said moveable cutting member so as to convert movement of the other of said lever ends into reciprocating movement of said moveable cutting member.

8. The surgical cutting instrument of claim 1 wherein said fixed and moveable cutting edges extend outward from a side of said fixed and moveable members and are arcuate in shape and are inclined toward one another sufficiently to provide a narrow initial overlapping cutting arc that progresses along the full arc.

9. The surgical cutting instrument of claim 1 wherein:

said moveable cutting edge is at an angle of about 45 degrees to the longitudinal axis of said moveable cutting member; and said fixed cutting is at an angle greater than the angle of said moveable cutting edge.

10. The surgical cutting instrument of claim 9 wherein said cutting edges are arcuate in shape at the outermost tip.

11. The surgical cutting instrument of claim 9 wherein said fixed cutting edge has a sharp point at the outermost tip.

12. The surgical cutting instrument of claim 9 wherein;

said fixed cutting member forms the outermost distal end of the cutting instrument; and said moveable cutting member has an outward travel overlapping said fixed cutting edge and terminating short of said outermost end.

13. A surgical cutting instrument comprising:

a housing;

an elongated fixed cutting member having proximal and distal ends and fixed at said proximal end to said housing, an axially directed fixed cutting edge on said a distal end directed toward said proximal end, and a recess adjacent said fixed cutting edge;

an elongated moveable tubular cutting member reciprocally mounted on said fixed cutting member and having distal and proximal ends, an axially extending moveable cutting edge formed on said distal end and extending away from said proximal end toward said fixed cutting edge, said moveable cutting member being movable into shearing engagement with said fixed cutting edge and having an axially directed passage therein defining an inlet opening in said distal end, said cutting edges of said fixed and moveable cutting members being angled toward one another and so configured as to initially overlap at a center portion to produce an initial concentrated shearing action and a continuing progressive shearing action on bone placed between said cutting edges to produce a chip of bone for each reciprocation of said first cutting member, wherein each said chip is deposited in said recess and moved into said passage through said opening and moves rearward with each reciprocation; and means on said housing for reciprocally moving said moveable cutting member with respect to said second cutting member in a first, forward direction and in a second, rearward direction.

14. The surgical cutting instrument of claim 3 further comprising sheath means on said housing covering at least a portion of said moveable cutting member so as to prevent damage to tissue in the region of the operation situs due to movement of said first cutting member, said sheath means not extending beyond the distal end of said second cutting member.

15. The surgical cutting instrument of claim 4 wherein said fixed and moveable cutting edges extend outward from a side of said fixed and moveable members and are angled toward one another and thereby provide a narrow initial cutting arc that progresses along the full arc.

16. The surgical cutting instrument of claim 15 wherein:

said moveable cutting edge is at an angle of about 45 degrees to the longitudinal axis of said moveable cutting member; and said fixed cutting is at an angle greater than the angle of said moveable cutting edge.

17. The surgical cutting instrument of claim 16 wherein said cutting edges are arcuate in shape at the outermost tip.

18. The surgical cutting instrument of claim 16 wherein said fixed cutting edge has a sharp point at the outermost tip.

19. The surgical cutting instrument of claim 18 wherein;

said fixed cutting member forms the outermost distal end of the cutting instrument; and said moveable cutting member has an outward travel overlapping said fixed cutting edge and terminating short of said outermost end.

* * * * *